(12) United States Patent
Niedermeyer

(10) Patent No.: US 9,883,670 B2
(45) Date of Patent: Feb. 6, 2018

(54) COMPOSITIONS AND METHODS FOR TREATING PLANT DISEASES

(71) Applicant: ATTOSTAT, INC., Salt Lake City, UT (US)

(72) Inventor: William Harold Niedermeyer, West Jordan, UT (US)

(73) Assignee: ATTOSTAT, INC., Salt Lake City, UT (US)

( * ) Notice: Subject to any disclaimer, the term of this patent is extended or adjusted under 35 U.S.C. 154(b) by 0 days.

(21) Appl. No.: 14/861,442

(22) Filed: Sep. 22, 2015

(65) Prior Publication Data

US 2016/0081347 A1   Mar. 24, 2016

Related U.S. Application Data

(60) Provisional application No. 62/054,215, filed on Sep. 23, 2014.

(51) Int. Cl.
*A01N 59/16* (2006.01)
*A01N 25/04* (2006.01)

(52) U.S. Cl.
CPC .................. *A01N 25/04* (2013.01)

(58) Field of Classification Search
None
See application file for complete search history.

(56) References Cited

U.S. PATENT DOCUMENTS

| | | | |
|---|---|---|---|
| 4,515,740 A | 5/1985 | Schuttenberg et al. | |
| 5,227,608 A | 7/1993 | Yoshida | |
| 5,390,864 A | 2/1995 | Alexander | |
| 5,585,020 A | 12/1996 | Becker et al. | |
| 6,509,070 B1 | 1/2003 | Voevodin et al. | |
| 7,014,737 B2 | 3/2006 | Harutyunyan et al. | |
| 7,332,351 B2 * | 2/2008 | Tan | A61K 49/183 252/301.4 R |
| 7,371,457 B2 | 5/2008 | Oldenburg et al. | |
| 7,374,730 B2 | 5/2008 | Simard et al. | |
| 7,384,560 B2 | 6/2008 | Martens et al. | |
| 7,509,993 B1 | 3/2009 | Turng et al. | |
| 7,553,801 B2 | 6/2009 | Alexander et al. | |
| 7,662,731 B2 | 2/2010 | Itoh et al. | |
| 7,682,970 B2 | 3/2010 | Grigoropoulos et al. | |
| 7,700,032 B1 | 4/2010 | Lu et al. | |
| 7,884,160 B2 | 2/2011 | Wang et al. | |
| 7,985,367 B2 | 7/2011 | Hiromatsu et al. | |
| 8,685,293 B1 | 4/2014 | Coppa et al. | |
| 2001/0031564 A1 | 10/2001 | Suzuki et al. | |
| 2003/0086859 A1 | 5/2003 | Kawakami et al. | |
| 2003/0102099 A1 | 6/2003 | Yadav et al. | |
| 2004/0214001 A1 | 10/2004 | Oldenburg et al. | |
| 2006/0142853 A1 | 6/2006 | Wang et al. | |
| 2007/0287202 A1 | 12/2007 | Maehashi et al. | |
| 2008/0035682 A1 | 2/2008 | Coffey et al. | |
| 2008/0161631 A1 | 7/2008 | Axtell et al. | |
| 2008/0263940 A1 | 10/2008 | Parish et al. | |
| 2008/0292673 A1 * | 11/2008 | Crudden | A01N 25/12 424/417 |
| 2009/0000186 A1 | 1/2009 | Sanders et al. | |
| 2009/0246530 A1 | 10/2009 | Murakami et al. | |
| 2010/0040655 A1 | 2/2010 | Ren et al. | |
| 2010/0050872 A1 | 3/2010 | Lee | |
| 2010/0068299 A1 * | 3/2010 | van der Krieken | A01N 41/04 424/638 |
| 2010/0072645 A1 | 3/2010 | Hiromatsu et al. | |
| 2010/0180413 A1 | 7/2010 | Jeong | |
| 2010/0183739 A1 | 7/2010 | Newman | |
| 2010/0187091 A1 | 7/2010 | Pierce et al. | |
| 2010/0196192 A1 | 8/2010 | Liu et al. | |
| 2011/0039078 A1 | 2/2011 | Brennan Fournet et al. | |
| 2011/0052460 A1 | 3/2011 | Coffey et al. | |
| 2011/0193025 A1 | 8/2011 | Ichikawa et al. | |
| 2011/0228890 A1 | 9/2011 | Dean et al. | |
| 2011/0244056 A1 * | 10/2011 | Santra | A01N 25/34 424/630 |
| 2012/0088066 A1 | 4/2012 | Aytug et al. | |
| 2012/0136164 A1 | 5/2012 | Ying et al. | |

(Continued)

FOREIGN PATENT DOCUMENTS

CN   102120619   7/2011
CN   103891558   7/2014

(Continued)

OTHER PUBLICATIONS

Badawy et al., "Surface Charge-Dependent Toxicity of Silver Nanoparticles", Environ. Sci. Technol. 2011, 45, 283-287.
U.S. Appl. No. 14/861,243, filed Sep. 22, 2015, Office Action dated Mar. 9, 2016.
U.S. Appl. No. 15/088,863, filed Apr. 1, 2016, Tarbet et al.
U.S. Appl. No. 15/098,071, filed Apr. 13, 2016, Tarrbet et al.
International Search Report for PCT App. No. PCT/US2012/044907 dated Jan. 31, 2013.
U.S. Appl. No. 14/861,318, filed Sep. 22, 2015, Office Action dated Apr. 25, 2016.
U.S. Appl. No. 14/861,318, filed Sep. 22, 2015, Notice of Allowance dated May 20, 2016.
U.S. Appl. No. 14/861,318, filed Sep. 22, 2015, Corrected Notice of Allowance dated Jun. 15, 2016.
U.S. Appl. No. 14/861,243, filed Sep. 22, 2015, Final Office Action dated Jul. 26, 2016.

(Continued)

*Primary Examiner* — Mina Haghighatian
*Assistant Examiner* — Luke Karpinski
(74) *Attorney, Agent, or Firm* — Workman Nydegger

(57) ABSTRACT

Nanoparticle compositions for treating citrus greening disease and other plant diseases include a liquid or gel carrier and metal nanoparticles dispersed therein. The metal nanoparticles can be spherical-shaped and/or coral-shaped. Methods of treating plant diseases include applying a nanoparticle composition to an infected plant part to kill the microbe causing the disease. The method may further include removing an infected plant part, such as a branch, treating the infected plant part with a nanoparticle composition, and grafting the plant part (branch) back onto the plant. The plant may particularly be a citrus tree.

21 Claims, 8 Drawing Sheets

(56) References Cited

U.S. PATENT DOCUMENTS

| | | | |
|---|---|---|---|
| 2012/0138862 A1 | 6/2012 | Hogan | |
| 2012/0164073 A1 | 6/2012 | Xu et al. | |
| 2012/0174472 A1 | 7/2012 | Mills | |
| 2012/0301531 A1 | 11/2012 | Uhlmann et al. | |
| 2013/0001833 A1* | 1/2013 | Niedermeyer | B82Y 40/00 264/400 |
| 2013/0334104 A1 | 12/2013 | Marsh | |
| 2014/0274830 A1 | 9/2014 | Pol et al. | |
| 2014/0288194 A1 | 9/2014 | Neidermeyer | |

FOREIGN PATENT DOCUMENTS

| | | |
|---|---|---|
| CN | 104014811 | 9/2014 |
| KR | 20060021749 | 8/2006 |
| WO | WO2013141879 | 9/2013 |

OTHER PUBLICATIONS

U.S. Appl. No. 14/298,598, filed Jun. 6, 2014, Neidermeyer.
U.S. Appl. No. 14/861,243, filed Sep. 22, 2015, Neidermeyer.
U.S. Appl. No. 14/861,318, filed Sep. 22, 2015, Neidermeyer.
U.S. Appl. No. 14/861,375, filed Sep. 22, 2015, Neidermeyer.
U.S. Appl. No. 14/861,500, filed Sep. 22, 2015, Neidermeyer.
U.S. Appl. No. 14/861,562, filed Sep. 22, 2015, Neidermeyer.
Chien et al., "Synthesis of nanoparticles: sunlight formation of gold nanodecahedra for ultra-sensitive lead-ion detection", Green Chem., vol. 13, pp. 1162-1166, May 2011.
International Search Report for PCT App. No. PCT/US2015/051642 dated Dec. 14, 2015.
International Search Report for PCT App. No. PCT/US2015/051638 dated Dec. 17, 2015.
International Search Report for PCT App. No. PCT/US2015/051640 dated Dec. 17, 2015.
International Search Report for PCT App. No. PCT/US2015/051643 dated Dec. 17, 2015.
International Search Report for PCT App. No. PCT/US2015/051649 dated Dec. 17, 2015.
International Search Report for PCT App. No. PCT/US2015/051646 dated Dec. 18, 2015.
Liu et al., "A novel coral-like porous SnO2 hollow architecture: biomimetic swallowing growth mechanism and enhanced photovoltaic property for dye-sensitized solar cell application", Chem. Commun., vol. 46, pp. 472-474, 2010.
U.S. Appl. No. 13/175,708, filed Jul. 1, 2011, Final Office Action dated Mar. 28, 2016.
Santos et al., "Enhancemetn of antibiotic effect via gold:silver-alloy nanoparticles", J. Nanopart Res (2012) 14:859, pp. 1-8.
U.S. Appl. No. 14/864,243, filed Sep. 22, 2015, Office Action dated Nov. 2, 2016.
U.S. Appl. No. 15/415,562, filed Jan. 25, 2017, Niedermeyer.
Prabhu et al., "Silver nanoparticles: mechanism of antimicrobial action, synthesis, medical applications, and toxicity effects", International Nano Letters, 2012, 2:32, pp. 1-10.
U.S. Appl. No. 14/861,562, filed Sep. 22, 2015, Office Action dated Dec. 7, 2016.
U.S. Appl. No. 14/861,243, filed Sep. 22, 2015, Final Office Action dated Jan. 27, 2017.
Barcikowski et al., "Generation of nanoparticle colloids by picosecond and femtosecond laser ablations in liquid flow", Appl. Phys. Lett. 91, 083113 (2007).
Jacobson, "These six diseases should worry you more than Ebola", Inside Energy Oct. 2014; [online] retrieved on Jan. 29, 2017 from http://www.pbs.org/newshour/updates/six-diseases-actually-worry/; 10 pages.
Jana et al., "Seeding Growth for Size Control of 5-40 nm Diameter Gold Nanoparticles", Langmuir 2001, 17, 6782-6786.
Mafuné et al., "Formation of Stable Platinum Nanoparticles by Laser Ablation in Water", J. Phys. Chem. B 2003, 107, 4218-4223.
Pal et al., "Does the Antibacterial Activity of Silver Nanoparticles Depend on the Shape of the Nanoparticle?", Applied and Environmental Microbiology, 2007; 73(6): 1712-1720.
Phuoc et al, "Synthesis of Ag-deoionized water nanofluids using multi-beam laser ablation in fluids", Optics and Lasers in Engineering 45 (2007) 1099-1106.
Rawashdeh et al., "Antibacterial Mechanisms of Metallic Nanoparticles: A Review", Dynamic Biochemistry, Process Biotechnology and Molecular Biology 2009 pp. 12-20.
Riabinina et al., "Influence of pressure on the Pt nanoparticle growth modes during pulsed laser ablation", Journal of Applied Physics 108, 034322 (2010, published online Aug. 12, 2010).
Sahu et al., "Flower Shaped Silver Nanostructures: An Efficient Bacteria Exterminator", A Search for Antibacterial Agents; Chapter 2; [online] retrieved from: http://www.intechopen.com/books/a-search-for-antibacterial-agents; 2007; 73(6): 1712-1720.
Sylvestre et al., "Surface Chemistry of Gold Nanoparticles Produced by Laser Ablation in Aqueous Media", J Phys. Chem. B 2004, 108, 16864-16869.
Sweeney et al., "Rapid Purification and Size Separation of Gold Nanoparticles via Diafiltration", J. Am. Chem. Soc. 2006, 128, 3190-3197 (Published on web Feb. 18, 2006).
U.S. Appl. No. 15/088,863, filed Apr. 1, 2016, Office Action dated Feb. 3, 2017.
U.S. Appl. No. 13/175,708, filed Jul. 1, 2011, Office Action dated Feb. 10, 2017.
U.S. Appl. No. 14/298,594, filed Jun. 6, 2014, Office Action dated Mar. 21, 2017.

* cited by examiner

COMPOSITIONS AND METHODS FOR TREATING PLANT DISEASES

CROSS-REFERENCE TO RELATED APPLICATIONS

This application claims the benefit of U.S. Provisional Patent Application No. 62/054,215, filed Sep. 23, 2014, the disclosure of which is incorporated herein in its entirety.

BACKGROUND

1. Field of the Invention

Disclosed herein are nanoparticle compositions and methods for treating plant diseases, such as citrus greening disease.

2. Relevant Technology

Plant diseases of many types threaten the world's food supply. Among the most devastating is citrus greening disease, which affects citrus trees, primarily orange trees. There is no cure for citrus greening disease and efforts to control the disease have been slow because infected citrus plants are difficult to maintain, regenerate, and study. The only known solution is to spray trees with insecticides to kill the insects responsible for spreading the disease. In June 2014, the United States Department of Agriculture allocated US $31.5 million for research to help combat citrus greening disease.

Citrus greening disease is distinguished by the common symptoms of yellowing of the veins and adjacent tissues of the citrus plant, followed by yellowing or mottling of the entire leaf, followed by premature defoliation, dieback of twigs, decay of feeder rootlets and lateral roots, and decline in vigor. This is ultimately followed by death of the entire plant. Affected trees have stunted growth, bear multiple off-season flowers (most of which fall off), and produce small, irregularly-shaped fruit with a thick, pale peel that remains green at the bottom. Fruit from these trees tastes bitter.

Citrus greening disease is caused by a vector-transmitted pathogen. The causative agents are motile bacteria, *Candidatus Liberibacter* spp. Transmission is by insects: the Asian citrus psyllid (Sternorrhyncha: Psyllidae), *Diaphorina citri* or, in Africa, by *Trioza erytreae*, the African citrus psyllid, also known as the 2-spotted citrus psyllid. The disease was first described in 1929 and first reported in China in 1943. The African variation was first reported in 1947 in South Africa, where it is still widespread.

The causative agents are fastidious phloem-restricted, gram-negative bacteria in the gracilicutes clade. The Asian form, *L. asiaticus* is heat tolerant. This means the greening symptoms can develop at temperatures of up to 35° C. The African form, *L. africanum*, is heat sensitive and in its case, symptoms only develop when the temperature is in the range 20-25° C. The bacteria are transmitted by the psyllid vectors and also by graft transmission. Although *Trioza erytreae* is the natural vector of African citrus greening and *Diaphorina citri* is the natural vector of Asian citrus greening, either psyllid can in fact transmit either of the greening agents under experimental conditions.

Researchers at the Agricultural Research Service have used lemon trees infected with citrus greening disease to infect periwinkle plants in an effort to study the disease. Periwinkle plants are easily infected with the disease and respond well when experimentally treated with antibiotics. Researchers are testing the effect of penicillin G sodium and biocide 2,2-dibromo-3-nitrilopropionamide as potential treatments for infected citrus plants based on preliminary results observed when applied to infected periwinkle.

Distribution of citrus greening disease is primarily in tropical and subtropical Asia. It has been reported in all citrus-growing regions in Asia except Japan. The disease has affected crops in China, Taiwan, India, Sri Lanka, Malaysia, Indonesia, Myanmar, Sri Lanka, the Philippines, Pakistan, Thailand, the Ryukyu Islands, Nepal, Saudi Arabia, and Afghanistan. Areas outside Asia have also reported the disease: Réunion, Mauritius, Brazil, and Florida (since 1998), and in several municipalities in Mexico since 2009. On Mar. 30, 2012, citrus greening disease was confirmed in a single citrus tree in Hacienda Heights, Calif. Prospects are dim for the ubiquitous backyard citrus orchards of California as residential growers are unlikely to consistently use the pesticides which provide effective control in commercial orchards.

Since the disease's detection in Florida City and Homestead, 90,000 acres of citrus groves have been wiped out. The high cost of spraying to kill off some of the psyllids is pushing some growers to the financial brink. The average cost of producing an acre of oranges is $1,800, nearly double what it cost in 1995. A 2012 analysis estimated the disease has cost growers $4.6 billion and resulted in the loss of about 8,000 jobs.

In the heyday of Florida citrus, around 1970, the number of acres with orange, grapefruit, and specialty fruit orchards surpassed 900,000. Today, it is reportedly slightly more than 500,000 acres.

Accordingly, there has been a long-felt but unsatisfied need to find a cure for citrus greening disease. The need to find a cure for citrus greening disease has become particularly acute as large numbers of citrus trees in the United States have been devastated. Notwithstanding many attempts to control the disease none have been particularly effective and none actually provide a reliable cure.

SUMMARY

Disclosed herein are nanoparticle compositions and methods for treating plant diseases caused by pathogens, such as bacteria and fungi, including, but not limited to, citrus greening disease infecting citrus plants. Also disclosed are methods for making the nanoparticle compositions.

In some embodiments, the nanoparticle composition comprises (1) a carrier that can be applied to a plant part and (2) a plurality of metal nanoparticles. By way of example, the nanoparticles can be solid spherical-shaped metal nanoparticles and/or coral-shaped metal nanoparticles in which each coral-shaped metal nanoparticle has a non-uniform cross section and a globular structure formed by multiple, non-linear strands joined together without right angles.

In some embodiments, the nanoparticle composition comprises spherical-shaped metal nanoparticles having a concentration in a range of about 10 ppb to about 100 ppm, or about 0.5 ppm to about 100 ppm, a mean particle size in a range of about 2 nm to about 25 nm, and a particle size distribution so that at least 99% of the metal nanoparticles have a particle size within 30% of the mean particle size. In addition, the nanoparticle composition can also comprise coral-shaped metal nanoparticles that can potentiate activity of the spherical-shaped metal nanoparticles.

In some embodiments, the metal nanoparticles can comprises at least one nonionic, ground state metal selected from the group consisting of gold, platinum, silver, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, and alloys thereof.

In some embodiments, a method of treating plant disease comprises: (1) applying a nanoparticle composition comprising a carrier and metal nanoparticles to a plant part; and (2) the nanoparticle composition killing or denaturing microbes in the plant or plant part. By way of example, the plant disease is citrus greening disease and the nanoparticle composition kills bacteria that cause citrus greening disease.

In some embodiments, a method of treating a plant disease comprises: (1) removing a diseased plant part; (2) treating the plant part by applying the nanoparticle composition onto or into the diseased plant part; and (3) grafting the treated plant part back onto the plant. By way of example, the plant comprises a citrus tree and the diseased plant part comprising a branch of the citrus tree. Advantageously, the metal nanoparticles selective kill bacteria causing citrus greening disease or other plant disease without harming humans who may contact a treated citrus tree or eat citrus fruit exposed to the metal nanoparticles.

These and other advantages and features of the invention will be set forth in part in the description which follows, and in part will become apparent to those skilled in the art upon examination of the following or may be learned by practice of the invention.

DETAILED DESCRIPTION OF THE PREFERRED EMBODIMENTS

Disclosed herein are nanoparticle compositions for treating plant disease and methods for treating plant diseases. In some embodiments, metal nanoparticles are dispersed within or contained on or within in a carrier that can be applied onto or into a plant or plant part. The carrier can be a liquid, gel or solid. The nanoparticle compositions can be formulated for treating citrus greening disease and other diseases, such as those caused by microbes.

Nanoparticle Configurations

In some embodiments, metal nanoparticles may comprise or consist essentially of nonionic, ground state metal nanoparticles. Examples include spherical-shaped metal nanoparticles, coral-shaped metal nanoparticles, or a blend of spherical-shaped metal nanoparticles and coral-shaped metal nanoparticles.

In some embodiments, metal nanoparticles useful for making nanoparticle compositions comprise spherical-shaped nanoparticles, preferably spherical-shaped metal nanoparticles having a solid core. The term "spherical-shaped metal nanoparticles" refers to nanoparticles that are made from one or more metals, preferably nonionic, ground state metals, having only internal bond angles and no external edges or bond angles. In this way, the spherical nanoparticles are highly resistant to ionization, highly stable, and highly resistance to agglomeration. Such nanoparticles can exhibit a high ξ-potential, which permits the spherical nanoparticles to remain dispersed within a polar solvent without a surfactant, which is a surprising and expected result.

In some embodiments, spherical-shaped metal nanoparticles can have a diameter of about 40 nm or less, about 35 nm or less, about 30 nm or less, about 25 nm or less, about 20 nm or less, about 15 nm or less, about 10 nm or less, about 7.5 nm or less, or about 5 nm or less. In some embodiments, spherical-shaped nanoparticles can have a particle size distribution such that at least 99% of the nanoparticles have a diameter within 30% of the mean diameter of the nanoparticles, or within 20% of the mean diameter, or within 10% of the mean diameter. In some embodiments, spherical-shaped nanoparticles can have a mean particle size and at least 99% of the nanoparticles have a particle size that is within ±3 nm of the mean diameter, ±2 nm of the mean diameter, or ±1 nm of the mean diameter. In some embodiments, spherical-shaped nanoparticles can have a ξ-potential of at least 10 mV, preferably at least about 15 mV, more preferably at least about 20 mV, even more preferably at least about 25 mV, and most preferably at least about 30 mV.

Figure 1:
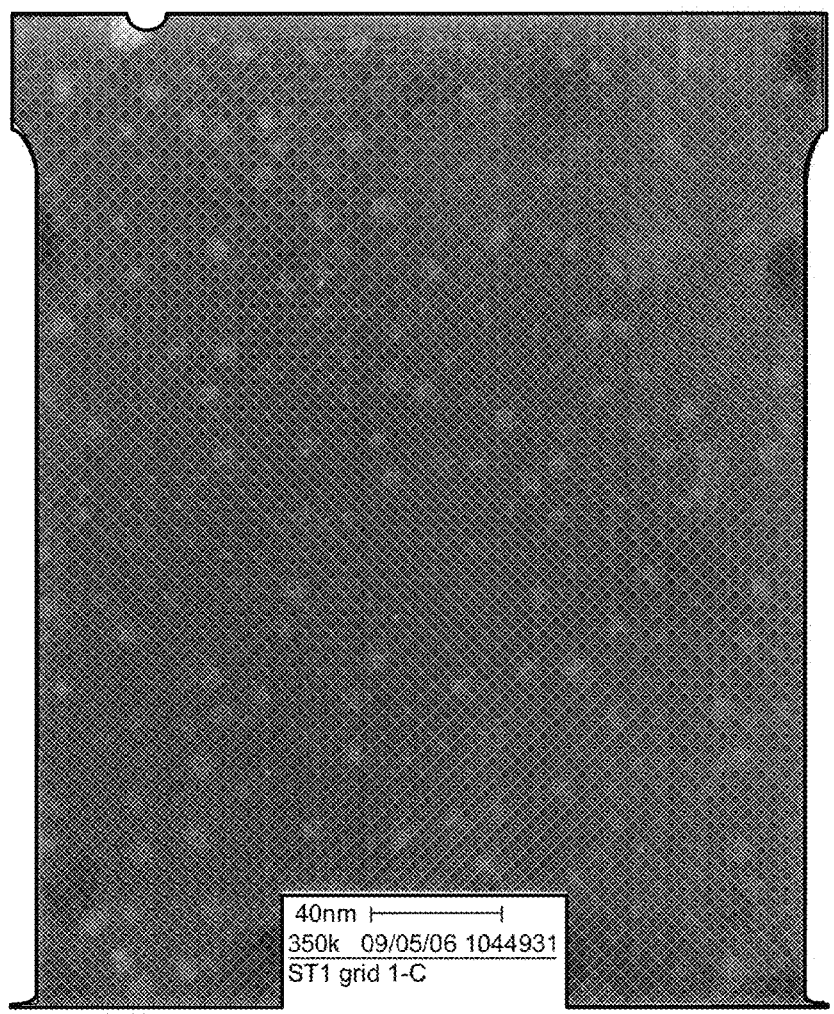
FIG. 1 is a transmission electron microscope image (TEM) of exemplary spherical-shaped metal nanoparticles having substantially uniform size and narrow particle size distribution for use in making nanoparticle compositions for treating plant disease.
Figure 2A:
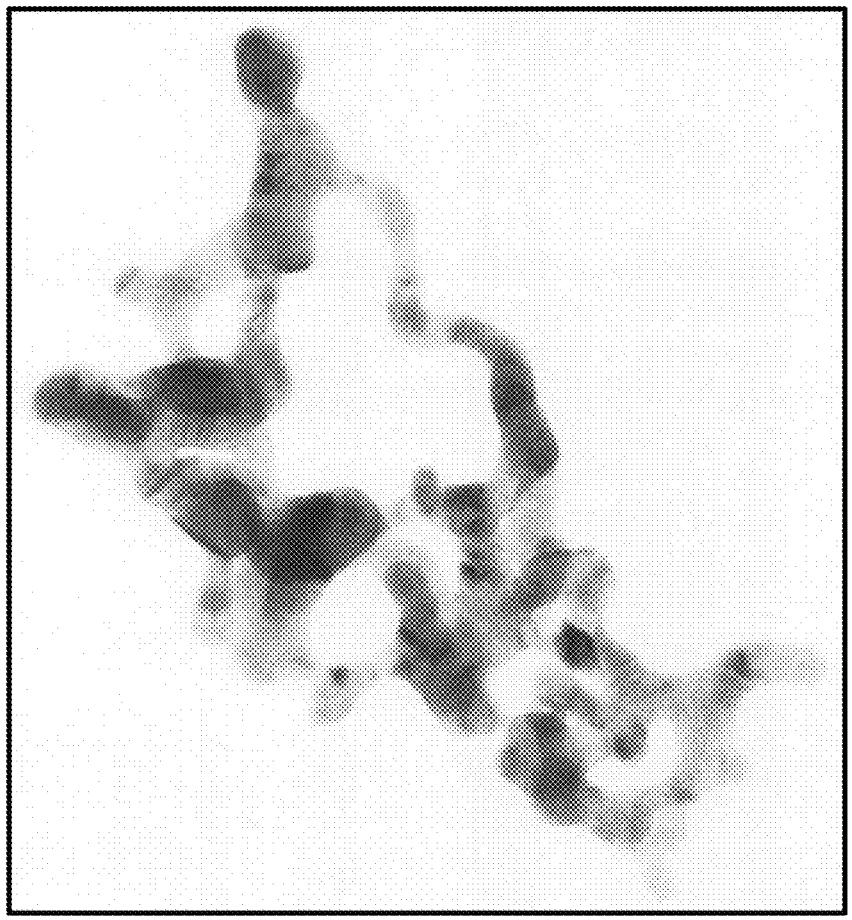
FIGS. 2A-2E are transmission electron microscope images (TEMs) of exemplary coral-shaped metal nanoparticles for use in making nanoparticle compositions for treating plant disease.
Figure 2B:
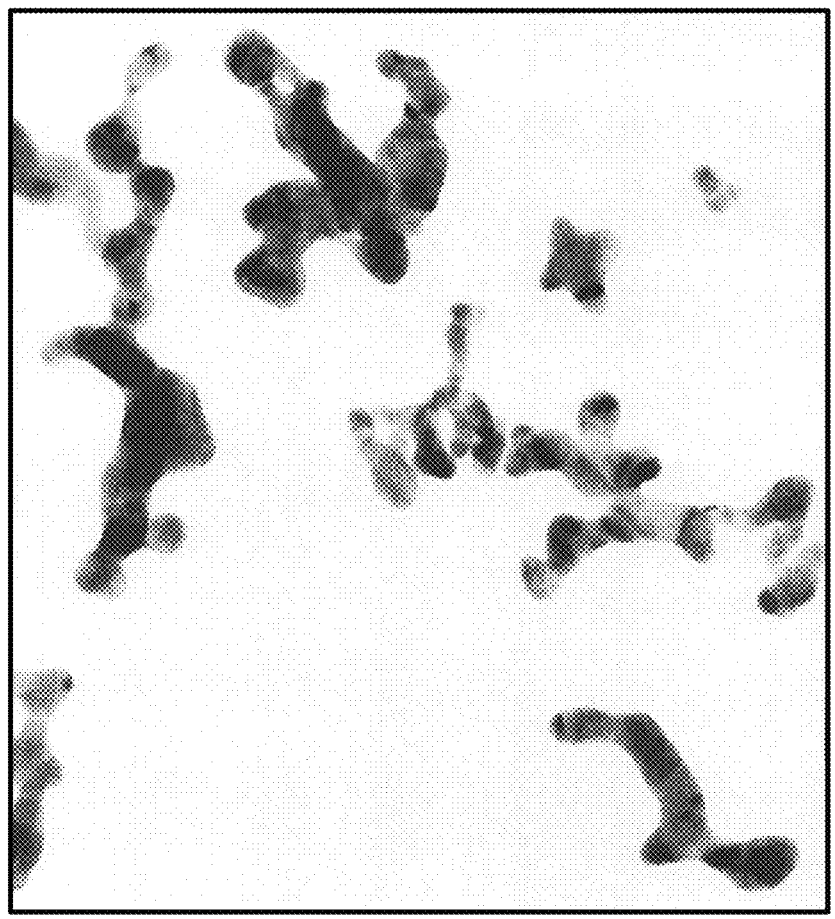
Figure 2C:
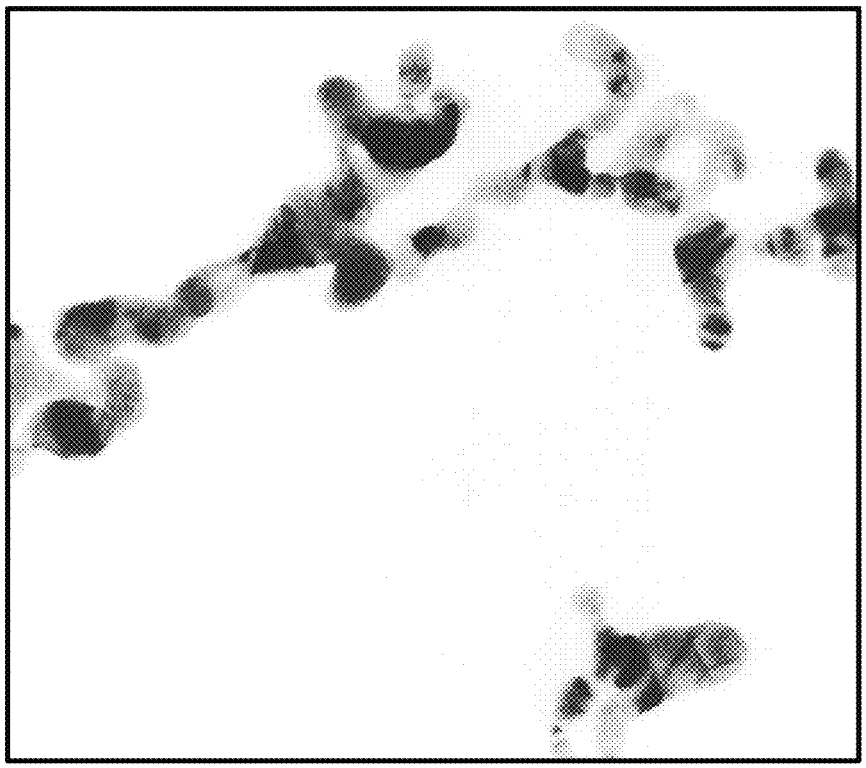
Figure 2D:
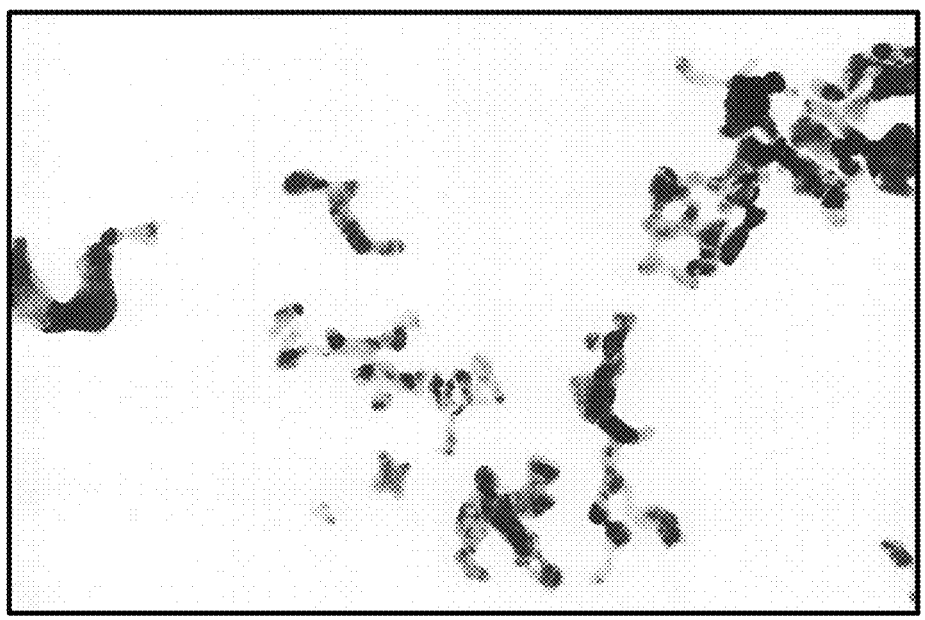
Figure 2E:
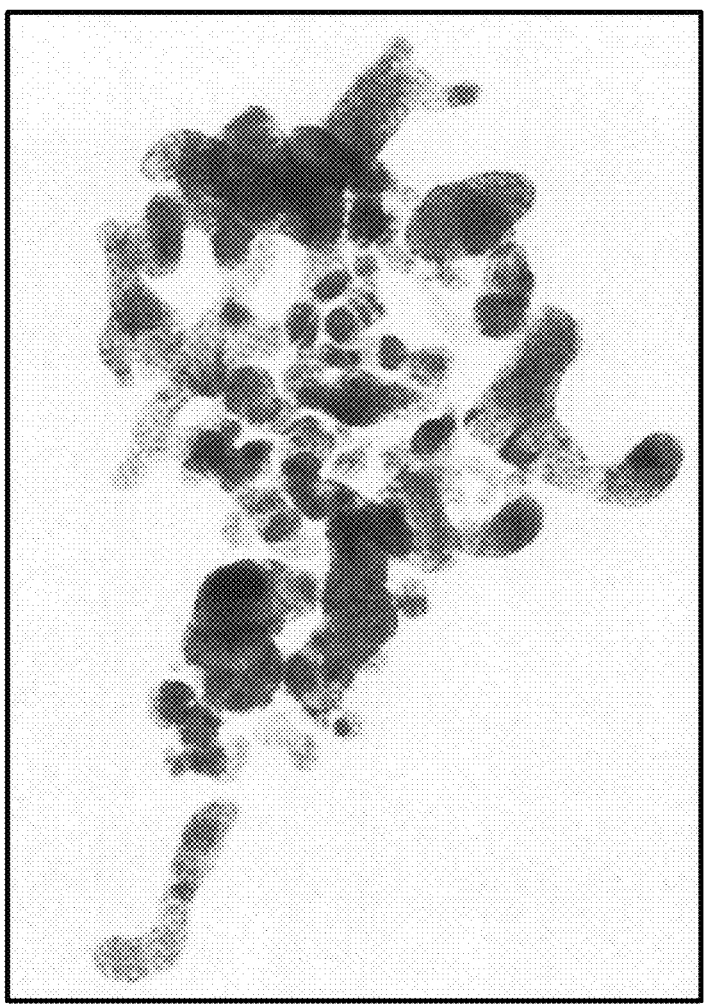

Examples of methods and systems for manufacturing spherical-shaped nanoparticles are disclosed in U.S. Pat. Pub. No. 2013/0001833 to William Niedermeyer (the "Niedermeyer Publication"), incorporated herein by reference. FIG. 1 is a transmission electron microscope image (TEM) of exemplary spherical-shaped nanoparticles made using the methods and systems of the Niedermeyer Publication. The illustrated nanoparticles are spherical-shaped silver (Ag) nanoparticles of substantially uniform size, with a mean diameter of about 10 nm and a narrow particle size distribution. In some embodiments, spherical-shaped nanoparticles can have a solid core rather than being hollow, as is the case with conventional metal nanoparticles, which are usually formed on the surfaces of non-metallic seed nanoparticles (e.g., silica), which are thereafter removed to yield hollow nanospheres.

In some embodiments, nonionic metal nanoparticles useful for making nanoparticle compositions may comprise coral-shaped nanoparticles. The term "coral-shaped metal nanoparticles" refers to nanoparticles that are made from one or more metals, preferably nonionic, ground state metals having a non-uniform cross section and a globular structure formed by multiple, non-linear strands joined together without right angles. Similar to spherical-shaped nanoparticles, coral-shaped nanoparticles may have only internal bond angles and no external edges or bond angles. In this way, coral-shaped nanoparticles can be highly resistant to ionization, highly stable, and highly resistance to agglomeration. Such coral-shaped nanoparticles can exhibit a high ξ-potential, which permits the coral-shaped nanoparticles to remain dispersed within a polar solvent without a surfactant, which is a surprising and expected result.

In some embodiments, coral-shaped nanoparticles can have lengths ranging from about 15 nm to about 100 nm, or about 25 nm to about 95 nm, or about 40 nm to about 90 nm, or about 60 nm to about 85 nm, or about 70 nm to about 80 nm. In some embodiments, coral-shaped nanoparticles can have a particle size distribution such that at least 99% of the nanoparticles have a length within 30% of the mean length, or within 20% of the mean length, or within 10% of the mean length. In some embodiments, coral-shaped nanoparticles can have a ξ-potential of at least 10 mV, preferably at least about 15 mV, more preferably at least about 20 mV, even more preferably at least about 25 mV, and most preferably at least about 30 mV.

Examples of methods and systems for manufacturing coral-shaped nanoparticles are disclosed in U.S. Provisional Application No. 62/054,126, filed Sep. 23, 2104, in the name of William Niedermeyer, (the "Niedermeyer Application"), which is incorporated herein by reference. FIGS. 2A-2E are transmission electron microscope images (TEMs) of exemplary coral-shaped metal nanoparticles made using the methods and systems of the Niedermeyer Application. The illustrated nanoparticles are coral-shaped gold nanoparticles.

Coral-shaped metal nanoparticles can be used instead of or in conjunction with spherical-shaped metal nanoparticles. In general, spherical-shaped metal nanoparticles can be smaller than coral-shaped metal nanoparticles and in this way can provide very high surface area for catalyzing desired reactions or providing other desired benefits. On the other hand, the generally larger coral-shaped nanoparticles can exhibit higher surface area per unit mass compared to spherical-shaped nanoparticles because coral-shaped nanoparticles have internal spaces and surfaces rather than a solid core and only an external surface. In some cases, providing nanoparticle compositions containing both spherical-shaped and coral-shaped nanoparticles can provide synergistic results. For example, coral-shaped nanoparticles can help carry and/or potentiate the activity of spherical-shaped nanoparticles in addition to providing their own unique benefits.

In some embodiments, the nanoparticle compositions may include both spherical-shaped and coral-shaped nanoparticles. In some embodiments, the mass ratio of spherical-shaped nanoparticles to coral-shaped nanoparticles in the nanoparticle composition can be in a range of about 1:1 to about 50:1, or about 2.5:1 to about 25:1, or about 5:1 to about 20:1, or about 7.5:1 to about 15:1, or about 9:1 to about 11:1, or about 10:1. The particle number ratio of spherical-shaped nanoparticles to coral-shaped nanoparticles in the nanoparticle composition can be in a range of about 10:1 to about 500:1, or about 25:1 to about 250:1, or about 50:1 to about 200:1, or about 75:1 to about 150:1, or about 90:1 to about 110:1, or about 100:1, Metal nanoparticles, including spherical-shaped and coral-shaped nanoparticles, may comprise any desired metal, mixture of metals, or metal alloy, including at least one of silver, gold, platinum, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, or alloys thereof.

Carriers

The nanoparticle composition also includes a carrier for delivering the metal nanoparticles to a plant or plant part. The carrier can be a liquid, gel, or solid. Some carriers may be more suitable than others depending on the plant being treated. For example, the solubility characteristics of the carrier can be selected to maximize or otherwise provide a desired diffusion throughout a treated plant part and/or another portion of the plant in contact the treated plant part.

Examples of carriers that can be used to formulate nanoparticle compositions as disclosed herein include, but are not limited to, water, alcohols, ketones, esters, turpentine, citrus oils, essential oils, vegetable oils, triglycerides, ethers, organic solvents, methanol, ethanol, isopropyl alcohol, other alcohols, glycols, glycerine, polyols, 1,3-propandiol, petroleum distillates, kerosene, waxes, polymers, polymerizable materials, and surfactants.

Gels known in the art can be used as carriers, such as gels containing one or more of the foregoing liquid components together with known gelling agents. Gel compositions can more easily adhere to a plant substrate being treated.

Solid carriers can be used for different reasons, such as to elute nanoparticles into a plant or plant part over time. Examples of solid carriers include, but are not limited to, polymers, rubbers, elastomers, foams, and gums. Depending on the characteristics of the plant to be treated and the desired rate of elution, one of skill in the art can select an appropriate solid carrier material.

In some embodiment, a nanoparticle composition can be formulated so that the metal nanoparticles are included in a concentration so that a measured quantity of the nanoparticle composition, when applied onto or into a plant or plant part, will provide a predetermined concentration or quantity of metal nanoparticles. The nanoparticle composition can have a higher concentration of nanoparticles that become diluted when mixed with other liquids applied to or naturally contained within the plant or plant part. Depending on the plant or plant part being treated, the nature of the nanoparticles being added, and the type of carrier being used, the nanoparticle composition may contain about 10 ppb to about 100 ppm, or about 0.5 ppm to about 100 ppm of metal nanoparticles by weight, or about 1 ppm to about 50 ppm, or about 2 ppm to about 25 ppm, or about 3 ppm to about 20 ppm metal nanoparticles by weight.

In some embodiments, the nanoparticle composition can also include one or more optional components or adjuvants to provide desired properties, including, but not limited to plant nutrients, fertilizer, insecticide, biocide, and/or mineral.

In some embodiments, the carrier may also function as, or may include, a stabilizing agent. For example, in some embodiments it may be desirable to have different specifically sized nanoparticles within the same solution to take advantage of each of the different properties and effects of the different particles. However, when differently sized particles are mixed into a single solution, the overall long-term stability of these particles within that single solution may be substantially diminished as a result of unequal forces exerted on the various particles causing eventual agglomeration of the particles. This phenomenon may become even more pronounced when that solution is either heated or cooled significantly above or below standard room temperature conditions.

Examples of stabilizing agents include alcohols (e.g., ethanol, propanol, butanol, etc.), polyphenols (e.g., arjuna bark extract, grape seed extract, etc.), mono-glycerides, di-glycerides, or triglycerides (e.g., grape seed oil, coconut oil, and the like), oils (e.g., lavender), other terpenes, amine compounds (e.g., mono-, di-, or tri-ethanol amine), carbohydrates (e.g., sucrose, fructose), liposomes, creams, other emulsions, and other polymers.

In some embodiments, stabilizing agents are dissolved within a separate carrier in the micro- to milli-molar concentration range with the upper range limitation typically being constrained not by efficacy but by product cost.

These various stabilizing agents have the capacity to hold at least two differently sized and/or shaped nanoparticles in suspension and deliver these nanoparticles into the treatment area of a plant or plant part without so powerfully retaining the nanoparticles so as to diminish the antimicrobial properties of the nanoparticles.

Antimicrobial Activity

Figure 3:
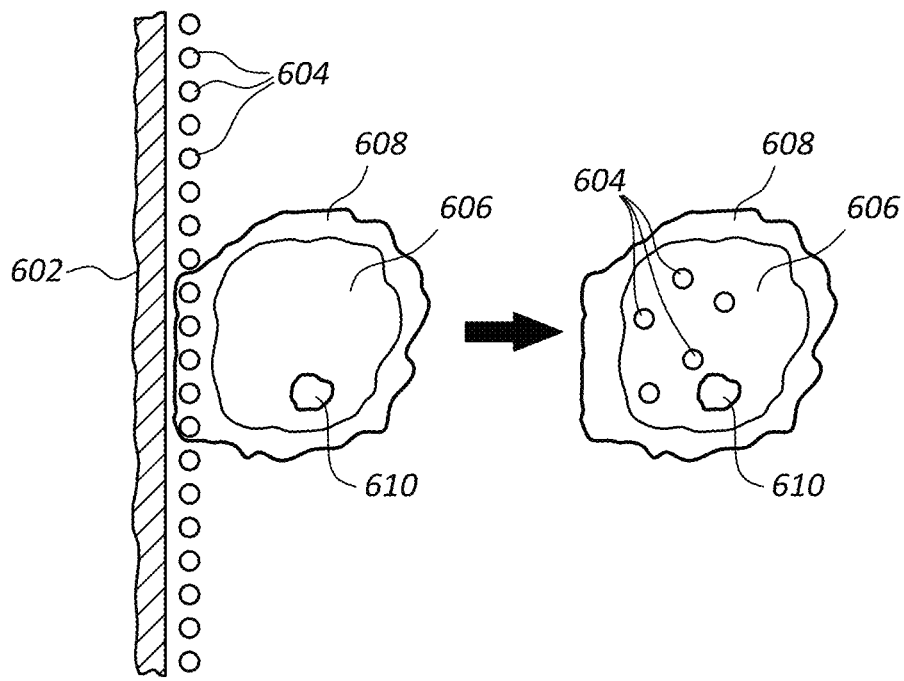
FIG. 3 schematically illustrates a microbe after having absorbed spherical-shaped metal nanoparticles.

FIG. 3 schematically illustrates a microbe 306 having absorbed spherical-shaped nanoparticles 304, such as by active absorption or other transport mechanism. The nanoparticles 304 can freely move throughout the interior of microbe 306 and come into contact with one or more vital proteins or enzymes 310 that, if denatured, will kill the microbe.

Figure 4:
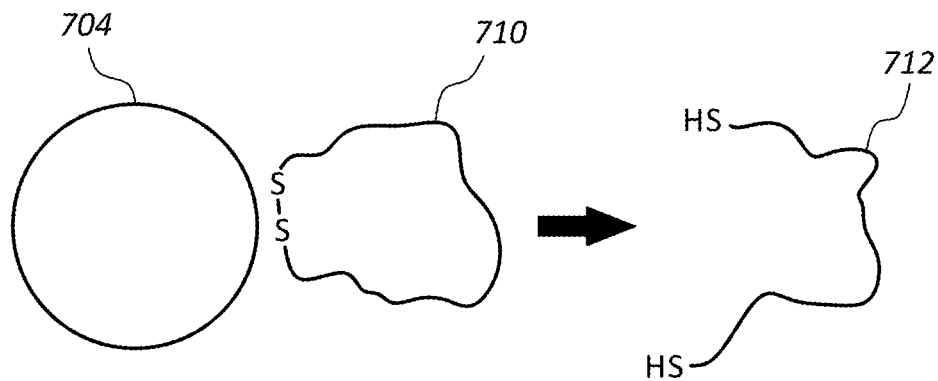
FIG. 4 schematically illustrates a microbe protein with disulfide bonds being catalytically denatured by an adjacent spherical-shaped nanoparticle.

One way that nanoparticles may kill or denature a microbe is by catalyzing the cleavage of disulfide (S—S) bonds within a vital protein or enzyme. FIG. 4 schematically illustrates a microbe protein or enzyme 410 with disulfide bonds being catalytically denatured by an adjacent spherical-shaped nanoparticle 404 to yield denatured protein or enzyme 412. In the case of bacteria or fungi, the cleavage of disulfide bonds and/or cleavage of other chemical bonds of vital proteins or enzymes may occur within the cell interior and thereby killing the microbe in this manner. Such catalytic cleavage of disulfide (S—S) bonds is facilitated by the generally simple protein structures of microbes, in which many vital disulfide bonds are on exposed and readily cleaved by catalysis.

Another mechanism by which metal (e.g., silver) nanoparticles can kill microbes is through the production of active oxygen species, such as peroxides, which can oxidatively cleave protein bonds, including but not limited to amide bonds.

In the case of viruses, spherical-shaped and coral-shaped metal nanoparticles can alternatively deactivate viruses by attaching to glycoproteins and/or catalyzing protein denaturing reactions in the protein coat so that the virus is no longer able to attach to a host cell and/or inject genetic material into the host cell. Because very small nanoparticles can pass through a virus, denaturing of the protein coat may occur within the interior of the virus. A virus that is rendered unable to attach to a host cell and/or inject genetic material into the host cell is essentially inactive and no longer pathogenic.

Figure 5:
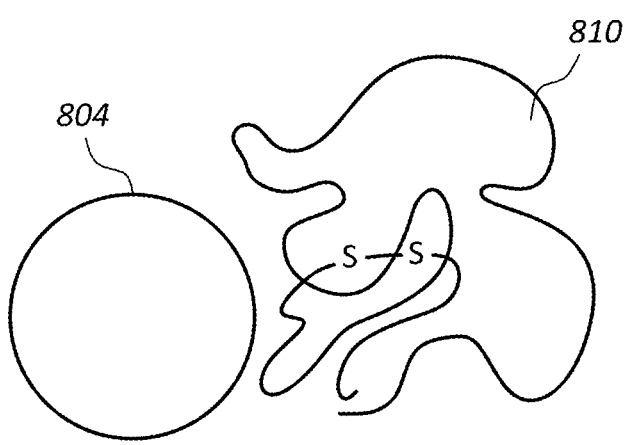
FIG. 5 schematically illustrates a mammalian protein with disulfide bonds that are shielded so as to resist being catalytically denatured by an adjacent spherical-shaped nanoparticle.

Notwithstanding the lethal nature of nonionic metal nanoparticles relative to microbes, they can be relatively harmless to humans, mammals, and healthy mammalian cells, which contain much more complex protein structures compared to simple microbes in which most or all vital disulfide bonds are shielded by other, more stable regions of the protein. FIG. 5 schematically illustrates a mammalian protein with disulfide (S—S) bonds that are shielded so as to resist being catalytically denatured by an adjacent spherical-shaped nanoparticle. In many cases the nonionic nanoparticles do not interact with or attach to human or mammalian cells, remain in and follow fluid flow, do not cross barriers, remain in the vascular system, and can be quickly and safely expelled through the urine without damaging kidneys or other cells.

In the particular case of silver (Ag) nanoparticles, the interaction of the silver (Ag) nanoparticle(s) within a microbe has been demonstrated to be particularly lethal without the need to rely on the production of silver ions ($Ag^+$) to provide the desired antimicrobial effects, as is typically the case with conventional colloidal silver compositions. The ability of silver (Ag) nanoparticles to provide effective microbial control without any significant release of toxic silver ions ($Ag^+$) into the surrounding environment is a substantial advancement in the art.

Microbe-Specific Nanoparticles

The size of the particles can be selected to target and kill specific types of microbes. For example, nanoparticle may be size optimized to selectively target and kill certain microbes. In the case of treating citrus greening disease, the nanoparticles can have a particle size in a range of about 1 nm to about 25 nm, or about 2 nm to about 15 nm, or about 2 nm to about 7 nm, or about 3 nm to about 6 nm, or about 7 nm to about 11 nm, or about 11 nm to about 14 nm.

By way of further example, nanoparticles having a diameter of less than about 9 nm (e.g., 1-7 nm or 3-6 nm) have been found to be effective in killing viruses, nanoparticles having a diameter of about 7 nm to about 12 nm (e.g., 8-10 nm) have been found to be effective in killing bacteria, and nanoparticles having a diameter of about 12 nm to about 18 nm (e.g., 12-15 nm) have been found to be effective in killing fungi. Within the foregoing ranges, there may be specific sizes of nanoparticles that are most effective in killing a particular type of virus, bacteria, or fungus. In some embodiments, nanoparticles effective in killing bacteria (e.g., having a diameter or about 7 nm to about 12 nm or from about 8 nm to about 10 nm) are included in a composition for treating citrus greening disease.

In some embodiments, spherical-shaped nanoparticles designed to selectively and preferentially deactivate bacteria can have a diameter of about 3 nm to about 14 nm, or about 5 nm to about 13 nm, or about 7 nm to about 12 nm, or about 8 nm to about 10 nm Within these size ranges it is possible to select "designer anti-bacterial particles" of specific size that are particularly effective in targeting a specific bacterium, such as bacteria responsible for citrus greening disease.

Treatment Methods

In some embodiments, a method of treating plant disease comprises: (1) applying a nanoparticle composition comprising a carrier and metal nanoparticles to a plant part; and (2) the nanoparticle composition killing or denaturing microbes in the plant or plant part. By way of example, the plant disease is citrus greening disease and the nanoparticle composition kills bacteria causing the citrus greening disease.

In some embodiments, a method of treating a plant disease comprises: (1) removing a diseased plant part; (2) treating the plant part by applying the nanoparticle composition onto or into the diseased plant part; and (3) grafting the treated plant part back onto the plant. By way of example, the plant comprises a citrus tree and the diseased plant part comprises a branch of the citrus tree. Advantageously, the metal nanoparticles selective kill bacteria causing citrus greening disease or other plant disease without harming humans who may contact a treated citrus tree or eat citrus fruit exposed to the metal nanoparticles.

Additionally, or alternatively, some embodiments include application of nanoparticles using one or more of trunk injection, micro-irrigation, foliate spraying, and/or transmission of nanoparticles by psyllids as they obtain nanoparticles from treated plants (e.g., citrus trees) and deliver them to the phloem of additional plants.

EXAMPLES

Examples 1-6

A diseased orange tree with citrus greening disease was treated as follows. First, a diseased branch was removed.

Second, the branch was soaked in a nanoparticle composition comprised of water and silver (Ag) nanoparticles for about 12-24 hours. Third, the nanoparticle treated branch was grafted back onto the tree. The effectiveness of the nanoparticle compositions was compared against ampicillin for effectiveness since ampicillin is known to kill bacteria that cause citrus greening. The nanoparticle compositions used in Examples 1-6 contained the silver nanoparticles having the characteristics in the table below.

| Example 1 | Nanoparticle Size (±1 nm) | Concentration |
|---|---|---|
| 1 | 3 nm | 1 ppm |
| 2 | 10 nm | 1 ppm |
| 3 | 14 nm | 1 ppm |
| 4 | 3 nm | 5 ppm |
| 5 | 10 nm | 5 ppm |
| 6 | 14 nm | 5 ppm |

All of the nanoparticle compositions were effective in killing at least some bacteria. The most effective nanoparticle composition was that of Example 4, containing 5 ppm of silver nanoparticles having a particle size of 3 nm, which was as effective as ampicillin. Moreover, the nanoparticle compositions were non-toxic to humans and the surrounding environment and left no trace of ionic nanoparticles. It is believed that providing non-ionic metal nanoparticles that do not readily form metal ions renders the nanoparticles essentially inert but for their ability to kill microbes that cause plant diseases.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of treating citrus greening disease, comprising:
applying a non-ionic nanoparticle composition comprising a liquid carrier and silver nanoparticles onto or into a citrus plant or citrus plant part, wherein the silver nanoparticles are formed by laser-ablation so as to be nonionic and spherical with no external bond angles or edges and have solid metal cores, a mean particle size in a range of about 1 nm to about 25 nm, and a narrow particle size distribution in which least 99% of the metal nanoparticles have a particle size within ±3 nm of the mean particle size; and
the nanoparticle composition killing or denaturing microbes in the citrus plant or citrus plant part that cause the citrus greening disease without release of silvers ions,
wherein the silver nanoparticles are non-toxic to humans or mammals and are effective in killing or denaturing microbes or bacteria that cause citrus greening disease.

2. A method as in claim 1, wherein the carrier comprises at least one member selected from the group consisting of water, alcohols, ketones, esters, turpentine, citrus oils, essential oils, vegetable oils, triglycerides, ethers, organic solvents, methanol, ethanol, isopropyl alcohol, other alcohols, glycols, glycerine, polyols, 1,3-propandiol, petroleum distillates, kerosene, waxes, polymers, polymerizable materials, and surfactants.

3. A method as in claim 1, wherein the silver nanoparticles comprise spherical-shaped nanoparticles.

4. A method as in claim 3, the nanoparticle composition further comprising coral-shaped nanoparticles having a particle size of about 15 nm to about 100 nm, each coral-shaped metal nanoparticle having a non-uniform cross section and a globular structure formed by multiple, non-linear strands joined together without right angles.

5. A method as in claim 4, wherein the coral-shaped metal nanoparticles have a mean length and wherein at least 99% of the coral-shaped metal nanoparticles have a length within 30% of the mean length.

6. A method composition as in claim 4, wherein the composition has a mass ratio of spherical-shaped nanoparticles to coral-shaped nanoparticles of about 5:1 to about 20:1.

7. A method as in claim 4, wherein composition has a particle number ratio of spherical-shaped nanoparticles to coral-shaped nanoparticles of about 50:1 to about 200:1.

8. A method as in claim 4, wherein the coral-shaped nanoparticles comprise at least one metal selected from the group consisting of gold, platinum, silver, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, and alloys thereof.

9. A method as in claim 1, wherein the nanoparticle composition further comprises gold nanoparticles.

10. A method as in claim 1, wherein the silver nanoparticles have a concentration in a range of about 10 ppb to about 100 ppm by weight of the nanoparticle composition.

11. A method as in claim 1, wherein the silver nanoparticles have a mean particle size in a range of about 2 nm to about 15 nm.

12. A method as in claim 1, the method comprising removing a diseased plant part from the citrus plant, treating the diseased plant part by applying the nanoparticle composition onto or into the diseased plant part, and grafting the treated plant part back onto the citrus plant.

13. A method as in claim 12, the citrus plant comprising a citrus tree and the plant part comprising a branch of the citrus tree.

14. A method as in claim 13, wherein the citrus tree is an orange tree.

15. A method as in claim 1, the silver nanoparticles selectively killing bacteria causing citrus greening disease without harming humans contacting the citrus tree or eating citrus fruit exposed to the silver nanoparticles.

16. A method of killing bacteria associated with citrus greening disease, comprising:
applying a non-ionic nanoparticle composition onto or into a citrus tree, the nanoparticle composition comprising a carrier and silver nanoparticles that are spherical and non-ionic with no external bond angles or edges, have solid metal cores and a mean particle size in a range of about 1 nm to about 25 nm, are non-toxic to humans or mammals, are effective in killing or denaturing bacteria that cause citrus greening disease, and have a concentration in a range of about 10 ppb to about 100 ppm by weight of the nanoparticle composition; and
the nanoparticle composition killing or denaturing bacteria on or in the citrus tree that cause citrus greening disease.

17. A method as in claim 16, wherein the citrus tree is an orange tree.

18. A method as in claim 16, the method comprising removing a branch of the citrus tree, treating the branch by applying the nanoparticle composition onto or into the branch, and grafting the branch back onto the citrus tree.

19. A method as in claim 16, wherein the silver nanoparticles are effective in killing or deactivating bacteria without release of silver ions.

20. A method as in claim 16, wherein the silver nanoparticles are provided in a dispersed form.

21. A method of killing bacteria associated with citrus greening disease, comprising:

applying a non-ionic nanoparticle composition onto or into a citrus plant, the nanoparticle composition comprising a carrier and silver nanoparticles made by laser ablation so as to be spherical-shaped with no external bond angles or edges and non-ionic so as to be effective in killing or denaturing bacteria that cause citrus greening disease while being non-toxic to humans or mammals, and so as to have a mean particle size of less than about 25 nm and in which at least 99% of the metal nanoparticles have a particle size within ±3 nm of the mean particle size; and the nanoparticle composition killing bacteria on or in the citrus tree that cause citrus greening disease.

* * * * *

UNITED STATES PATENT AND TRADEMARK OFFICE
CERTIFICATE OF CORRECTION

PATENT NO. : 9,883,670 B2
APPLICATION NO. : 14/861442
DATED : February 6, 2018
INVENTOR(S) : William Harold Niedermeyer Page 1 of 2

It is certified that error appears in the above-identified patent and that said Letters Patent is hereby corrected as shown below:

On the Title Page

Item (56), OTHER PUBLICATIONS, Column 2:
Change "U.S. Appl. No. 15/098,071, filed April 13, 2016, Tarrbet et al." to –U.S. Appl. No. 15/098,071, filed April 13, 2016, Tarbet et al.–

Item (56), Page 2, U.S. PATENT DOCUMENTS, Column 1:
Change "2014/0288194 A1 9/2014 Neidermeyer" to –2014/0288194 A1 9/2014 Niedermeyer–

Item (56), Page 2, FOREIGN PATENT DOCUMENTS, Column 1:
Change "KR 2006021749 8/2006" to –KR 2006021749 3/2006–

Item (56), Page 2, OTHER PUBLICATIONS, Column 1:
Change "U.S. Appl. No. 14/298,598 filed June 6, 2014, Neidermeyer." to –U.S. Appl. No. 14/298,594 filed June 6, 2014, Niedermeyer.–
Change "U.S. Appl. No. 14/861,243 filed September 22, 2015, Neidermeyer." to –U.S. Appl. No. 14/861,243, filed September 22, 2015, Niedermeyer.–
Change "U.S. Appl. No. 14/861,318 filed September 22, 2015, Neidermeyer." to –U.S. Appl. No. 14/861,318, filed September 22, 2015, Niedermeyer.–
Change "U.S. Appl. No. 14/861,375 filed September 22, 2015, Neidermeyer." to –U.S. Appl. No. 14/861,375, filed September 22, 2015, Niedermeyer.–
Change "U.S. Appl. No. 14/861,500 filed September 22, 2015, Neidermeyer." to –U.S. Appl. No. 14/861,500, filed September 22, 2015, Niedermeyer.–
Change "U.S. Appl. No. 14/861,562 filed September 22, 2015, Neidermeyer." to –U.S. Appl. No. 14/861,562, filed September 22, 2015, Niedermeyer.–
Change "Santos et al; "Enhancemetn of antibiotic effect via gold:silver-alloy nanoparticles", J. Nanopart Res (2012) 14:859, pp. 1-8." to –Santos et al; "Enhancement of antibiotic effect via gold:silver-alloy nanoparticles", J. Nanopart Res (2012) 14:859, pp. 1-8.–

Signed and Sealed this
Third Day of July, 2018

Andrei Iancu
*Director of the United States Patent and Trademark Office*

CERTIFICATE OF CORRECTION (continued)
U.S. Pat. No. 9,883,670 B2

In the Specification

<u>Column 3</u>
Line 56, remove [in]

<u>Column 4</u>
Line 10, change "resistance" to –resistant–
Line 13, change "expected" to –unexpected–
Line 61, change "resistance" to –resistant–
Line 65, change "expected" to –unexpected–

<u>Column 5</u>
Line 67, change "contact the" to –contact with the–

<u>Column 6</u>
Line 21, change "embodiment" to –embodiments–

<u>Column 7</u>
Line 8, change "306" to –606–
Line 9, change "304" to –604–
Line 11, change "304" to –604–
Line 12, change "306" to –606–
Line 13, change "310" to –610–
Line 18, change "410" to –710–
Line 20, change "404" to –704–
Line 21, change "412" to –712–
Line 27, remove [on]

<u>Column 8</u>
Line 5, change "nanoparticle" to –nanoparticles–
Line 23, change first instance of "or" to –of–